US011110132B2

(12) United States Patent
McGwire

(10) Patent No.: US 11,110,132 B2
(45) Date of Patent: Sep. 7, 2021

(54) LIVE ATTENUATED PARASITIC VACCINE

(71) Applicant: Ohio State Innovation Foundation, Columbus, OH (US)

(72) Inventor: Bradford McGwire, Columbus, OH (US)

(73) Assignee: Ohio State Innovation Foundation, Columbus, OH (US)

(*) Notice: Subject to any disclaimer, the term of this patent is extended or adjusted under 35 U.S.C. 154(b) by 0 days.

(21) Appl. No.: 16/675,842

(22) Filed: Nov. 6, 2019

(65) Prior Publication Data

US 2020/0147148 A1 May 14, 2020

Related U.S. Application Data

(60) Provisional application No. 62/758,412, filed on Nov. 9, 2018.

(51) Int. Cl.

| | |
|---|---|
| ***A61K 35/68*** | (2006.01) |
| ***A61K 39/005*** | (2006.01) |
| ***C12N 1/10*** | (2006.01) |
| *A61K 39/00* | (2006.01) |

(52) U.S. Cl.

CPC ............ *A61K 35/68* (2013.01); *A61K 39/005* (2013.01); *C12N 1/10* (2013.01); *A61K 2039/522* (2013.01)

(58) Field of Classification Search

None

See application file for complete search history.

(56) References Cited

U.S. PATENT DOCUMENTS 7,780,969 B2 * 8/2010 Tarleton ............... A61K 39/005 424/269.1
7,786,288 B2 * 8/2010 Karp ........................ A61P 43/00 536/23.72
10,188,733 B2 * 1/2019 von Andrian .......... A61K 39/00
2005/0084490 A1 * 4/2005 Adams .................... A61P 35/04 424/144.1
2012/0189581 A1 * 7/2012 Schultz-Cherry ............................ A61K 39/0208 424/93.1
2012/0328626 A1 * 12/2012 Sethuraman ....... C07K 16/1027 424/159.1
2020/0147148 A1 * 5/2020 McGwire ................. C12N 1/10

OTHER PUBLICATIONS

Rascher et al, Biochemical Journal, 1998, 334:650-667 (Year: 1998).*
Agallou et al, PLoS ONE 11(2): e0149894. doi:10.1371/journal.pone.0149894. Published Feb. 23, 2016 (Year: 2016).*
Bua et al, 2001, FEMS Microbiology Letters, 2001, 200:43-47. First published online: May 11, 2001 (Year: 2001).*
Bua et al, 2008, Parasitology, 135:217-228, (Year: 2008).*
Jha et al, American Journal of Tropical Medicine and Hygiene, Nov. 2019, 101/5 Supp. Supplement, pp. 20. Abstract No. 62 (Year: 2019).*
Kulkarni et al, JBC, Mar. 22, 2013, vol. 288, No. 12, pp. 8772-8784. (Year: 2013).*
Pelle et al Gene 2002, 290:181-191. (Year: 2002).*
Santos-Gomes et al, Vaccine 2014, 32:1247-1253. Available online Jan. 28, 2014 (Year: 2014).*
Venugopal et al, Acta. Cryst., 2007, F63:60-64 (Year: 2007).*
Breton et al, Infection and Immunity, Oct. 2005, 73/10:6372-6382. (Year: 2005).*
Cornelissen et al, FEMS Immunology and Medical Microbiology, 1996, 15:61-72. (Year: 1996).*
Jose da Silva et al, Brazilian Journal of Microbiology, 2014, 45/4:111-1129. (Year: 2014).*
Zofou et al, Infectious Diseases of Poverty, 2014, 3:1, 14 pages. (Year: 2014).*

* cited by examiner

*Primary Examiner* — Nita M. Minnifield
(74) *Attorney, Agent, or Firm* — Thomas|Horstemeyer LLP

(57) ABSTRACT

Disclosed herein is an avirulent live vaccine that involves a recombinant protozoan from the order Trypanosomatida having a knocked out or silenced cyclophilin gene, wherein the cyclophilin gene comprises *T. cruzi* cyclophilin 19 (TcCyp19) gene, or an orthologue thereof. Also disclosed is a method or inducing a protective immune response in a subject that involves administering to the subject a vaccine disclosed herein. Also disclosed is a method of treating or preventing Chagas disease, African trypanosomiasis, and/or leishmaniasis in a subject that involves administering to the subject a vaccine disclosed herein.

9 Claims, 11 Drawing Sheets

Specification includes a Sequence Listing.

| DPI | m-1 | m-2 | m-3 | m-4 | m-5 |
|---|---|---|---|---|---|
| 30 | 1 | 1 | 1 | 1 | 0 |
| 40 | 1 | 1 | 1 | 0 | 0 |
| 50 | 0 | 0 | 0 | 0 | 0 |

LIVE ATTENUATED PARASITIC VACCINE

CROSS-REFERENCE TO RELATED APPLICATIONS

This application claims benefit of U.S. Provisional Application No. 62/758,412, filed Nov. 9, 2018, which is hereby incorporated herein by reference in its entirety.

STATEMENT REGARDING FEDERALLY SPONSORED RESEARCH OR DEVELOPMENT

This invention was made with Government Support under Grant No. A1131227 awarded by the National Institutes of Health. The Government has certain rights in the invention.

SEQUENCE LISTING

This application contains a sequence listing filed in electronic form as an ASCII.txt file entitled "321501-1120 Sequence Listing_ST25" created on Nov. 6, 2019. The content of the sequence listing is incorporated herein in its entirety.

BACKGROUND

Human infection by the protozoan parasite *Trypanosoma cruzi* causes Chagas disease which is the leading infectious cause of heart failure in Latin America. Approximately 30% of those chronically infected develop cardiac fibrosis and associated cardiomyopathy. The Chagas disease is increasingly found outside of Latin America mainly due to migration of chronically infected individuals and at least 300,000 people in the United States and 6-7 million worldwide. Identification and treatment of infected people is challenging and only two rather antiquated drugs (nifurtimox and benznidazole) are available to treat the infection but are ineffective to completely clear the parasites from the host and are have significant side effects which hamper their use. Thus there is an urgent need to identify important parasite molecules for drug targets and develop newer more effective drugs to treat Chagas disease and to develop a vaccine for prevention of *T. cruzi* infection.

SUMMARY

Using a double knock-out (DKO) *Trypanosoma cruzi* parasite line devoid of cylclophilin 19 (Cyp19) expression, Cyp19 was identified as an indispensable protein for parasite infectivity and virulence, indicating that this protein represents a valuable target for inhibitors to treat infection. In addition, the DKO line is able to stimulate anti-parasitic immunity making it a suitable vaccine strain for parasitic infections.

Disclosed herein is an avirulent live vaccine that involves a recombinant protozoan from the order Trypanosomatida having a knocked out or silenced cyclophilin gene, wherein the cyclophilin gene comprises *T. cruzi* cyclophilin 19 (TcCyp19) gene, or an orthologue thereof.

In some embodiments, the protozoan is a *Trypanosoma* spp., such as *Trypanosoma cruzi* or *Trypanosoma brucei*. In some embodiments, the protozoan is a *Leishmania* spp.

The cyclophilin gene can be knocked out or silenced using standard methods. In some cases, the protozoan contains a double knockout of the cyclophilin gene. In some embodiments, the protozoan contains an inactivating mutation in the cyclophilin gene(s).

In some case, the disclosed vaccine can also be used as a vector to deliver other vaccine or immunotherapy antigens. Therefore, in some embodiments, the disclosed vaccine further comprises a heterologous gene expressing an immunogen, such as a viral or bacterial antigen.

Also disclosed is a method or inducing a protective immune response in a subject that involves administering to the subject a vaccine disclosed herein. In some embodiments, the vaccine is protective against the protozoan used to produce the live vaccine. In other embodiments, based on the high homology in the cyclophilin genes, the vaccine is cross-protective against other protozoan in the genus, e.g. other *Trypanosoma* spp. or *Leishmania* spp. In still other embodiments, the vaccine is cross-protective against other protozoan in the order Trypanosomatida.

In some embodiments, the disclosed vaccine is able to prophylactically prevent, delay, or reduce the severity of a parasitic infection. In other embodiments, the disclosed vaccine is able to treat an existing parasitic infection.

Therefore, also disclosed is a method of treating or preventing Chagas disease, African trypanosomiasis, and/or leishmaniasis in a subject that involves administering to the subject a vaccine disclosed herein.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 4A shows survival of DKO-immunized mice according to regimen in FIG. 3B, and non-immunized control mice infected (IP) with $10^5$ WT Brazil strain *T. cruzi*. FIG. 4B shows parasitemia assessment of mice (n=4 per group). Control mice were assessed just prior to death and DKO-immunized mice were analyzed at week 5 post-infection. Values are mean−/+standard deviation. Hpf=high powered field.

DETAILED DESCRIPTION

Figure 1B:
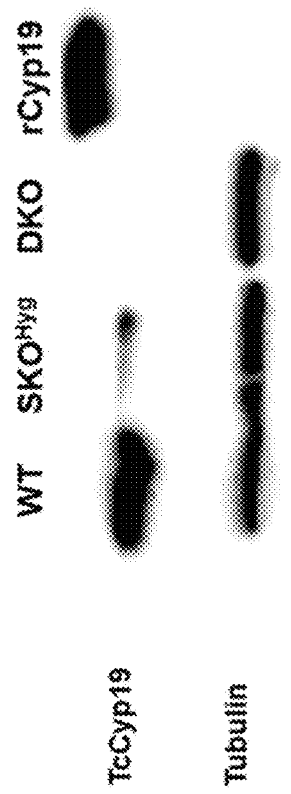
FIG. 1B shows results from a western blot analysis of the WT, single (SKO) and double (DKO) knock out lines using a-Cyp10 polyclonal Ab which shows that the DKO mutant is completely devoid of Cyp19 expression.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of chemistry, biology, and the like, which are within the skill of the art.

The following examples are put forth so as to provide those of ordinary skill in the art with a complete disclosure and description of how to perform the methods and use the probes disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms “a,” “an,” and “the” include plural referents unless the context clearly dictates otherwise.

The term “attenuated” as used herein describes a recombinant protozoa exhibiting a detectable reduction in infectivity or virulence in vitro or in vivo as compared to that of the parent strain of protozoa from which the recombinant protozoa is derived. Reduction in virulence encompasses any detectable decrease in any attribute of virulence, including infectivity in vitro or in vivo, or any decrease in the severity or rate of progression of any clinical symptom or condition associated with infection.

The term “orthologue” refers to genes in different species that share a common ancestral gene and, as used herein, encode a protein with the same function.

The term “subject” refers to any individual who is the target of administration or treatment. The subject can be a vertebrate, for example, a mammal. Thus, the subject can be a human or veterinary patient. The term “patient” refers to a subject under the treatment of a clinician, e.g., physician.

The term “therapeutically effective” refers to the amount of the composition used is of sufficient quantity to ameliorate one or more causes or symptoms of a disease or disorder. Such amelioration only requires a reduction or alteration, not necessarily elimination.

The term “pharmaceutically acceptable” refers to those compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio.

The term “treatment” refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

The term "prevent" refers to a treatment that forestalls or slows the onset of a disease or condition or reduced the severity of the disease or condition. Thus, if a treatment can treat a disease in a subject having symptoms of the disease, it can also prevent that disease in a subject who has yet to suffer some or all of the symptoms.

The term "percent (%) sequence identity" or "homology" is defined as the percentage of nucleotides or amino acids in a candidate sequence that are identical with the nucleotides or amino acids in a reference nucleic acid sequence, after aligning the sequences and introducing gaps, if necessary, to achieve the maximum percent sequence identity. Alignment for purposes of determining percent sequence identity can be achieved in various ways that are within the skill in the art, for instance, using publicly available computer software such as BLAST, BLAST-2, ALIGN, ALIGN-2 or Megalign (DNASTAR) software. Appropriate parameters for measuring alignment, including any algorithms needed to achieve maximal alignment over the full-length of the sequences being compared can be determined by known methods.

The term "recombinant" is generally used to indicate that the material (e.g., a protozoan, a nucleic acid, a genetic construct or a protein) has been altered by technical means (i.e., non-naturally) through human intervention. As used herein, the term denotes material (e.g., a protozoan, a nucleic acid, a genetic construct or a protein) that has been altered by technical means of mutagenesis.

The term "vaccine" as used herein, refers to a pharmaceutical composition that includes a live attenuated protozoan. A vaccine can include components in addition to the live attenuated protozoan, such as, for example, one or more adjuvants, a carrier, etc.

Disclosed herein is an avirulent live vaccine that involves a recombinant protozoan from the order Trypanosomatida having a knocked out or silenced cyclophilin gene, wherein the cyclophilin gene comprises *T. cruzi* cyclophilin 19 (TcCyp19) gene, or an orthologue thereof.

*Trypanosoma cruzi* has a family of ubiquitous and highly conserved proteins named cyclophilins that mediate protein folding events, catalyzing the interconversion of the cis and trans isomers of peptidyl-prolyl bonds in peptides and proteins (peptidyl-prolyl cis-trans isomerase (PPIase) activity), an enzymatic activity inhibited by the immunosuppressive undecapeptide Cyclosporin A (CsA). This cyclic peptide has a conformational polymorphism, given by a dependence of its structure and dynamics on the solution environment, that allows it to more readily move through a lipid bilayer and ensures its membrane permeability, increasing its therapeutic potential.

The herein disclosed recombinant protozoan has a gene corresponding to the *T. cruzi* cyclophilin of 19 kDa (TcCyp19) that is either knocked out or silenced. This homologue can be identified in the selected protozoan using routine methods. For example, the *T. cruzi* cyclophilin of 19 kDa (TcCyp19) has a 72% protein sequence identity with the human CyPA, and shows a high sequence identity with other Trypanosomatids of sanitary importance, as *Trypanosoma brucei* (90%) and *Leishmania* spp. (79-81%).

In some embodiments, the cyp19 gene is the TcCyp19 gene and has the nucleic acid sequence

```
                                    (SEQ ID NO: 1, Accession No. AF191832)
   1  gctatattgg gtagctcagt gagcatttta catctttcta aaagggaatt aatttattaa
  61  caacacacaa tgtcgtacaa gccgcatcac gccaccgtac cgaccaaccc gaaggtcttc
 121  ttcgacgtca gcattggtgg ccaatcagcc ggacgtgttg tcttcgagct cttcgccgac
 181  gccgttccca agacggctga gaacttccgg gcactttgca ccggtgagaa gaactttggc
 241  tacgctggaa gcggctttca tcgcattatc cccccagttca tgtgccaggg gggtgacttc
 301  accaatcaca acggcactgg cggcaggtct atctacggtg agaaatttgc cgacgagtcc
 361  tttgctggca aggctggcaa gcacttcggc ctcggtacgc tttccatggc gaatgctggc
 421  ccaaatacta acggctccca gttctttatt tgcactgcac ccacacagtg gcttgacggc
 481  aagcatgtcg tctttggcca ggtgctggaa ggcattgaag tcgttaaggc aatggaagcc
 541  gttggctccc agacgggcaa gacgagcaag ccggtgaaga ttgaggcctc tggtcaactt
 601  taaactgctc ttccggcaga gctttgaatg gacaaataac cggaaaagaa gggtacgggg
 661  aggagggacc aaaattagat taatccaaga accagaaaag aaaggaaaag gaaagaaaag
 721  agaaaaaaga aataatatga gaaaatgaga ataacgaggg tgtgaaaatc tgacttaaca
 781  gatccagccc gtgagatggc aataaggcag gaggcaaagc gagaaaaagc gtgctctcac
 841  gcctaagaaa gagggaagaa gagaggaagg tggagaaaaa tttcttaagg gtctgaaaaa
 901  agggagaggg ggaaaaaaaa aagatgaaga caaaggaaaa aaggggctaa aacgcggaaa
 961  aaaaaaagta caggaagaag tggactcatg tgcacccagg agggaaaaaa aaagggaatt
1021  gaatggccat gtacttcttg cctaattatt ttgctgttgg gtttttatta aaaaaaaaaa
1081  aaaaaaaaaa aaaaagtt,
```

or an orthologue or variant thereof having at least 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identity to SEQ ID NO:1.

In some embodiments, the cyp19 gene encodes the amino acid sequence

```
                    (SEQ ID NO: 2, Accession No. AAF05985)
MSYKPHHATVPTNPKVFFDVSIGGQSAGRVVFELFADAVPKTAENFRA

LCTGEKNFGYAGSGFHRIIPQFMCQGGDFTNHNGTGGRSIYGEKFADE

SFAGKAGKHFGLGTLSMANAGPNTNGSQFFICTAPTQWLDGKHVVFGQ

VLEGIEVVKAMEAVGSQTGKTSKPVKIEASGQL,
```

or a orthologue or variant thereof having at least 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identity to SEQ ID NO:2.

In some embodiments, the cyp19 gene is the *T. brucei* cyPA (TbCypA) gene and has the nucleic acid sequence

```
                                     (SEQ ID NO: 3, Accession No. U68270)
   1    aactaacgct attattagaa cagtttctgt actatattgg tcgttgaaac cacctatacc

  61    tatactattt cgcataagat gtcatacagg ccccaccacg caactgtacc caccaatccc

 121    aaggtgtact ttgatgtgag cattgcaggt caggcagccg gccgcatcac ctttgagctc

 181    ttcgctgacg ccgtaccaaa gacggcggag aacttccgtg cgttatgcac tggtgagaag

 241    ggcttcgggt acgccggcag cggctttcat cgcatcattc cgcaattcat gtgccaaggt

 301    ggtgacttca ctcgccacaa tggcacatgc ggcaagtcca tctatggtga aaagttcccc

 361    gatgaaagct tcgccggaaa ggcgggtaaa cacttcggcg ctggcacgct ttccatggcc

 421    aacgctggcc ccaacacgaa cggttcccag ttcttcattt gcacggctcc cactcagtgg

 481    cttgacggca aacacgtcgt cttcggtcag gtgcttgaag gcatggacgt cgtcaaggca

 541    atggaagctg tcggctcgca aggggaagc acaagcaagc ccgtcaagat tgactcgtgc

 601    ggccaactat aagagagcac gtagaggcgt gcacatgcaa catgaaatta cgctccgatc

 661    ccactgcttc ccccccctcc ccgtactgat acacgcacag cgaacaccga ctaattttt

 721    tttccctcaa gagtgcaagt tgaaaagggg aaaagcaagc agtaaagggg acaaaggaga

 781    ttattaaaag cagaggagca aataaaaaaa aaagaaatga aatgaataag caaaagaaaa

 841    tctctggctt ccaaatgaaa aaggaaaaga agaaaacata tggtacgtca tattctttga

 901    ggacggtttg ctggagaaaa gaacaaataa atgacaattt cttatggtta aagaaaaaga

 961    agaagaaaga aacagaagat agagaattgt cataaataag tgaaagatgg gaggggacaa

1021    agtaattaag tgggagtcat actgcgggga gtaccacaag gggaaaaatg ctagggatga

1081    aacgaaa,
```

or a orthologue or variant thereof having at least 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identity to SEQ ID NO:3.

In some embodiments, the cyp19 gene encodes the amino acid sequence

```
                            (SEQ ID NO: 4, Accession No. AAB07896),
MSYRPHHATVPTNPKVYFDVSIAGQAAGRITFELFADAVPKTAENFR

ALCTGEKGFGYAGSGFHRIIPQFMCQGGDFTRHNGTCGKSIYGEKFP

DESFAGKAGKHFGAGTLSMANAGPNTNGSQFFICTAPTQWLDGKHVV

FGQVLEGMDVVKAMEAVGSQGGSTSKPVKIDSCGQL
```

or a orthologue or variant thereof having at least 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identity to SEQ ID NO:4.

Recombinant DNA techniques for gene replacement or gene knockout are known in the art and include, but are not limited to, those that take advantage of homologous recombination. For example, cells of a pathogenic strain of protozoa may be transformed or transfected with a vector, such as a plasmid, comprising homologous nucleotide sequences that normally flank, or are located within, the disclosed cylophilin gene in a pathogenic strain of protozoa. Between or within the homologous nucleotide sequences, the vector may further comprise a nucleotide sequence that corresponds to the nucleotide sequence in the pathogenic strain but which is defective as a result, for example, of a "non-silent" change or deletion in one or more nucleotides compared to the sequence from the pathogenic strain. Transformation of a cell of the pathogenic strain with the vector is followed by integration of the defective gene sequence into the protozoa genome, which also serves to replace the original or "wild-type" sequence. Thus, the targeted gene is disabled in the transformed cell. Transformed cells may then be screened for those cells that exhibit an attenuated pathogenicity.

To aid in the selection of transformants, the vector may be engineered to further comprise a coding sequence for a reporter gene product or other selectable marker. Reporter genes which may be useful are well-known in the art and include, for example, the gene encoding chloramphenicol acetyl transferase (CAT), or the gene encoding luciferase. A further non-limiting example of a reporter gene is a sequence encoding *E. coli* β-galactosidase, which can be inserted into the vector and used to confirm transformants by detecting enzymatic activity through conversion of a substrate such as, for example, red-β-D-galactopyranoside, to a colored product.

Coding sequences that encode selectable markers which may be useful are also well-known in the art, and include those that encode gene products conferring resistance to antibiotics or anti-metabolites, or that supply an auxotrophic requirement. Examples of such sequences include those that confer resistance to hygromycin, or to neomycin, or to phleomycin.

Any coding sequence for a reporter gene product or selectable marker may be inserted into the vector in operative association with a regulatory element coding sequence. As used herein, a "regulatory element" includes, but is not limited to, inducible and non-inducible promoters, enhancers, operators and other elements known in the art that serve to drive and/or regulate expression. Also, as used herein, a DNA coding sequence is in "operative association" with one or more regulatory elements where the regulatory elements effectively regulate and allow for the transcription of the DNA coding sequence and/or the translation of the corresponding mRNA.

Once an appropriate vector is constructed, it is used to transform or transfect one or more cells from a parental strain of protozoa. The vector may be introduced into the cells in accordance with known techniques, including but not limited to electroporation, microinjection, viral transfection, liposome-mediated transfection, microprojectile bombardment, etc.

Once the vector is introduced into the protozoa cells, the presence, integration and maintenance of the introduced coding sequence into the host cell genome, or episomally, can be confirmed and monitored by standard techniques including, but not limited to, Southern hybridization analysis; PCR analysis, including reverse transcriptase-PCR (RT-PCR); immunological or colorimetric assay for the expected protein product; detecting the presence or absence of a marker gene function, such as appearance of a novel auxotrophy; or by detecting an attenuation in pathogenicity.

In some embodiments, the cyclophilin gene is silenced by introducing one or more inactivating mutations. Techniques for introducing mutations into nucleic acids are well-known to the skilled person and include, for example, but without limitation site-directed mutagenesis by PCR, homologous recombination, restriction enzyme digestion, ligation, CRISPR/Cas-9 etc. Standard reference works setting forth the general principles of recombinant DNA technology include Molecular Cloning: A Laboratory Manual, 2nd ed., vol. 1-3, ed. Sambrook et al., Cold Spring Harbor Laboratory Press, Cold Spring Harbor, N.Y., 1989; Current Protocols in Molecular Biology, ed. Ausubel et al., Greene Publishing and Wiley-Interscience, New York, 1992 (with periodic updates); Innis et al., PCR Protocols: A Guide to Methods and Applications, Academic Press: San Diego, 1990. For further description of CRISPR/Cas-9, see US20100076057A1, WO2010075424A2, WO2013126794A1, WO2013142578, WO2013169398, WO2013176772A1, US2013181440A1, US20140017214A1, WO2014011237A1, WO2014022702A2, WO2014071219A1, U.S. Pat. No. 8,697,359B1, and WO2014018423A2.

Disclosed herein are vaccines against infection from protozoa, such as the trypanosomatids disclosed herein, comprising an immunologically effective amount of the avirulent protozoa disclosed herein.

Also disclosed herein are methods for preparing a vaccine that protects a mammal against protozoan infection, comprising modifying cells from a pathogenic protozoa, such as the trypanosomatids disclosed herein; selecting and clonally propagating those modified cells that exhibit attenuated pathogenicity but which are capable of triggering an immune response in the mammal that protects against protozoan infection when administered in a live vaccine; and combining an immunologically effective amount of the attenuated cells with a pharmaceutically acceptable carrier in a form suitable for administration as a live vaccine to the subject.

Also disclosed herein are methods of vaccinating a subject against protozoan infection, comprising administering to the subject an immunologically effective amount of the disclosed vaccine.

The disclosed vaccine comprises live cells of an attenuated protozoa either as the sole antigenic component or in combination with one or more other antigens that trigger an immune response that protects a subject against a disease or pathological condition which may or may not be related to protozoan infection. Thus, also disclosed are combination vaccines, comprising an immunologically effective amount of disclosed avirulent recombinant protozoa; one or more other antigens that trigger an immune response that protects the subject against a disease or a pathological condition; and a pharmaceutically acceptable carrier. The combination vaccines may further comprise one or more other components including, for example, an adjuvant.

The vaccine is conventionally administered parenterally, for example, either by subcutaneous or intramuscular injection. However, the vaccine may also be administered by intraperitoneal or intravenous injection, or by other routes, including orally, intransally, rectally or vaginally, and where the vaccine is so administered, a veterinarily acceptable carrier is appropriately selected. The vaccine may simply comprise attenuated cells in culture fluid, which are administered directly to the subject. Alternatively, the vaccine may comprise attenuated cells combined with a pharmaceutically acceptable carrier selected from those known in the art based on the route of administration and its ability to maintain cell viability. Non-limiting examples of such carriers include water, saline, buffered vehicles and the like.

The vaccine may further comprise one or more other components such as an immunomodulatory agent including, for example, interleukin-1, or another immuno-enhancing substance such as a pharmaceutically acceptable adjuvant. Non-limiting examples of adjuvants include Freund's complete and incomplete adjuvants, mineral gels including, for example, aluminum hydroxide, and oil-in-water or water-in-oil formulations. Immunomodulatory agents are selected based on their ability to maintain both viability of the attenuated protozoan cells and ability of the cells to trigger a protective immune response in the vaccinated mammal.

An effective dosage may be determined by conventional means, starting with a low dose of attenuated cells and then increasing the dosage while monitoring the effects, and systematically varying the dosage as well. Numerous factors may be taken into consideration when determining an optimal dosage per subject. Primary among these is the species, the size of the subject, the age of the subject, the general condition of the subject, the presence of other drugs in the subject, the virulence of a particular strain of protozoa against which the animal is being vaccinated, and the like.

Vaccine regimens are selected also based on the above-described factors. Subjects may be vaccinated at any time. Supplemental administrations, or boosters, may be required for full protection. One method of detecting whether adequate immune protection has been achieved is to determine seroconversion and antibody titers in the subject after vaccination. Effective vaccination may require only a primary vaccination, or a primary vaccination with one or more booster vaccinations. Booster vaccinations may be administered at any time after primary vaccination depending, for example, on the immune response after primary vaccination, the severity of the outbreak, the virulence of the strain of protozoa causing the outbreak, the health of the vaccinate, etc. The timing of vaccination and the number of boosters, if any, may be determined by a clinician based on analysis of all relevant factors, some of which are described above.

In some embodiments, the concentration of attenuated cells in the vaccine ranges from about $1\times10^3$/ml to about $1\times10^8$/ml, including from about $2\times10^6$/ml to about $2\times10^7$/ml. A suitable dosage size ranges from about 0.5 ml to about 1.0 ml.

The disclosed vaccine protects a subject against infection or disease caused by protozoa. The term "protection" is used broadly and is not limited to absolute prevention of infection by protozoa, but includes a reduction in parasatemia, or in the severity of a disease or condition resulting from parasatemia, including a detectable reduction in one or more of the pathological effects or symptoms resulting from parasatemia, or a detectable reduction in the rate of progression of one or more of such pathological effects or symptoms. The disclosed vaccine of the invention is also preferably safe, i.e., it does not cause disease or significant side effects in the vaccinated subject.

Also disclosed is a method of treating or preventing Chagas disease, African trypanosomiasis, and/or leishmaniasis in a subject that involves administering to the subject a vaccine disclosed herein.

Chagas disease, also known as American trypanosomiasis, is a tropical parasitic disease caused by the protist *Trypanosoma cruzi*. It is spread mostly by insects known as Triatominae, or "kissing bugs". The symptoms change over the course of the infection. In the early stage, symptoms are typically either not present or mild, and may include fever, swollen lymph nodes, headaches, or local swelling at the site of the bite. After 8-12 weeks, individuals enter the chronic phase of disease and in 60-70% it never produces further symptoms. The other 30-40% of people develop further symptoms 10-30 years after the initial infection, including enlargement of the ventricles of the heart in 20-30%, leading to heart failure. An enlarged esophagus or an enlarged colon may also occur in 10% of people.

African trypanosomiasis, also known as sleeping sickness, is an insect-borne parasitic disease of humans and other animals. It is caused by protozoa of the species *Trypanosoma brucei*. There are two types that infect humans, *Trypanosoma brucei* gambiense (TbG) and *Trypanosoma brucei* rhodesiense (TbR). TbG causes over 98% of reported cases. Both are usually transmitted by the bite of an infected tsetse fly and are most common in rural areas.

Leishmaniasis is a disease caused by parasites of the *Leishmania* genus. It is spread by the bite of certain types of sandflies. The disease can present in three main ways: cutaneous, mucocutaneous, or visceral leishmaniasis. The cutaneous form presents with skin ulcers, while the mucocutaneous form presents with ulcers of the skin, mouth, and nose, and the visceral form starts with skin ulcers and then later presents with fever, low red blood cells, and enlarged spleen and liver. Infections in humans are caused by more than 20 species of *Leishmania*. Risk factors include poverty, malnutrition, deforestation, and urbanization. All three types can be diagnosed by seeing the parasites under the microscope. Additionally, visceral disease can be diagnosed by blood tests. Visceral disease is usually caused by *Leishmania donovani, L. infantum*, or *L. chagasi*, but occasionally these species may cause other forms of disease. The cutaneous form of the disease is caused by more than 15 species of *Leishmania*.

The disclosed vaccines can be used in combination with other agents suitable for treating or preventing protozoan infections. For example, drugs used to treat Chagas disease, trypanosomiasis, and leishmaniasis include azole or nitro derivatives, such as benznidazole or nifurtimox, pentamidine, suramin, eflornithine, and combinations thereof, such as nifurtimox-eflornithine combination treatment.

The disclosed vaccines can also be used with various antibiotics, steroids, analgesics, anti-inflammatory agents, anti-histaminic agents, or any combination thereof.

A number of embodiments of the invention have been described. Nevertheless, it will be understood that various modifications may be made without departing from the spirit and scope of the invention. Accordingly, other embodiments are within the scope of the following claims.

EXAMPLES

Figure 1A:
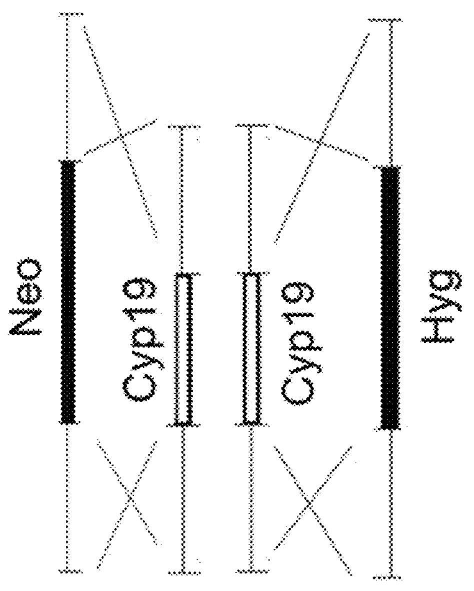
FIG. 1A illustrates a double allelic replacement strategy.
Figure 1C:
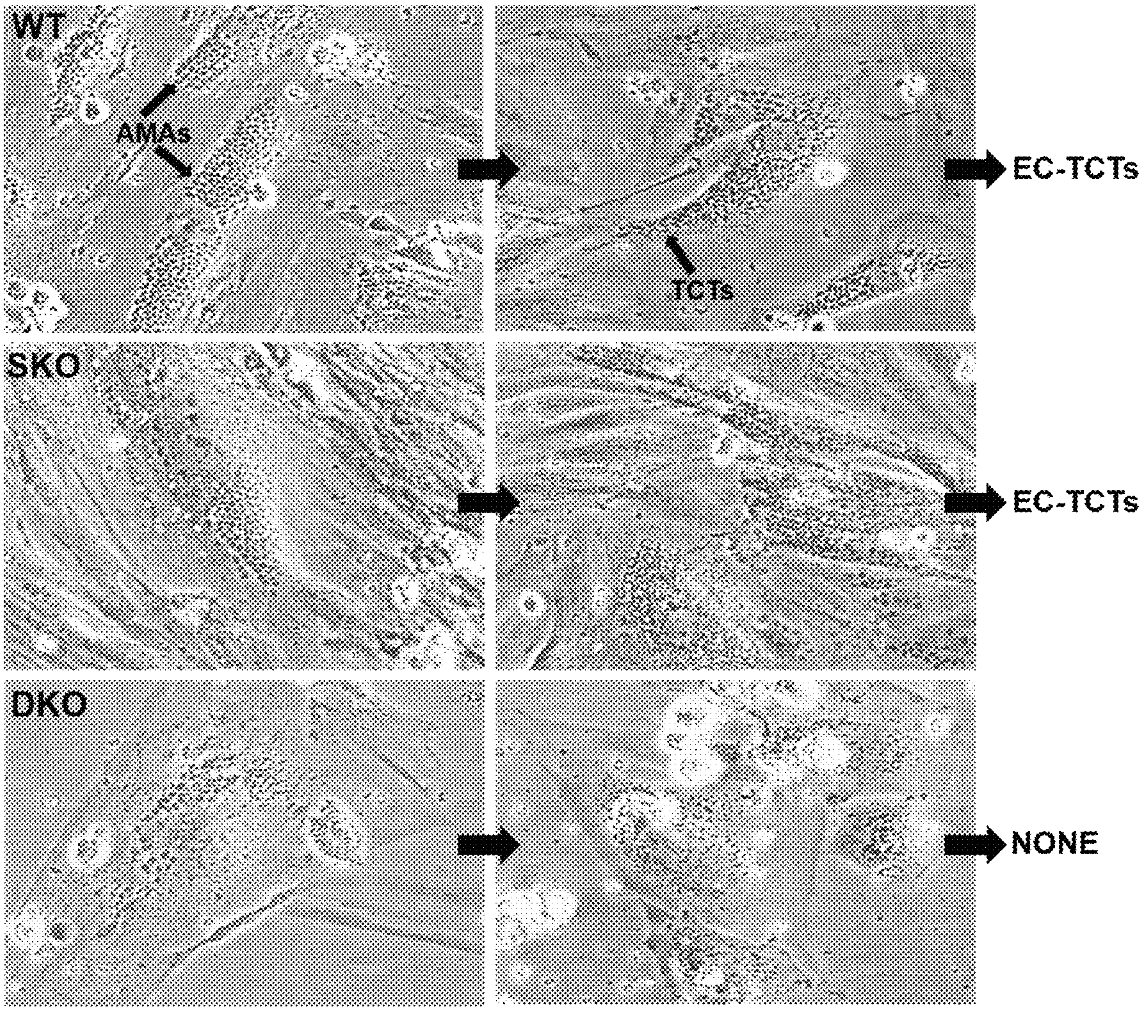
FIG. 1C shows monolayers of rat heart myoblasts infected with WT and SKO parasites develop into intracellular amastigotes (AMAs, indicated with arrows) while DKO line fails to replicate intracellularly or transform into and escape as extracellular trypomastigotes (EC-TCTs). The amastigotes ultimately degenerate inside the cytoplasm.
Figure 2A:
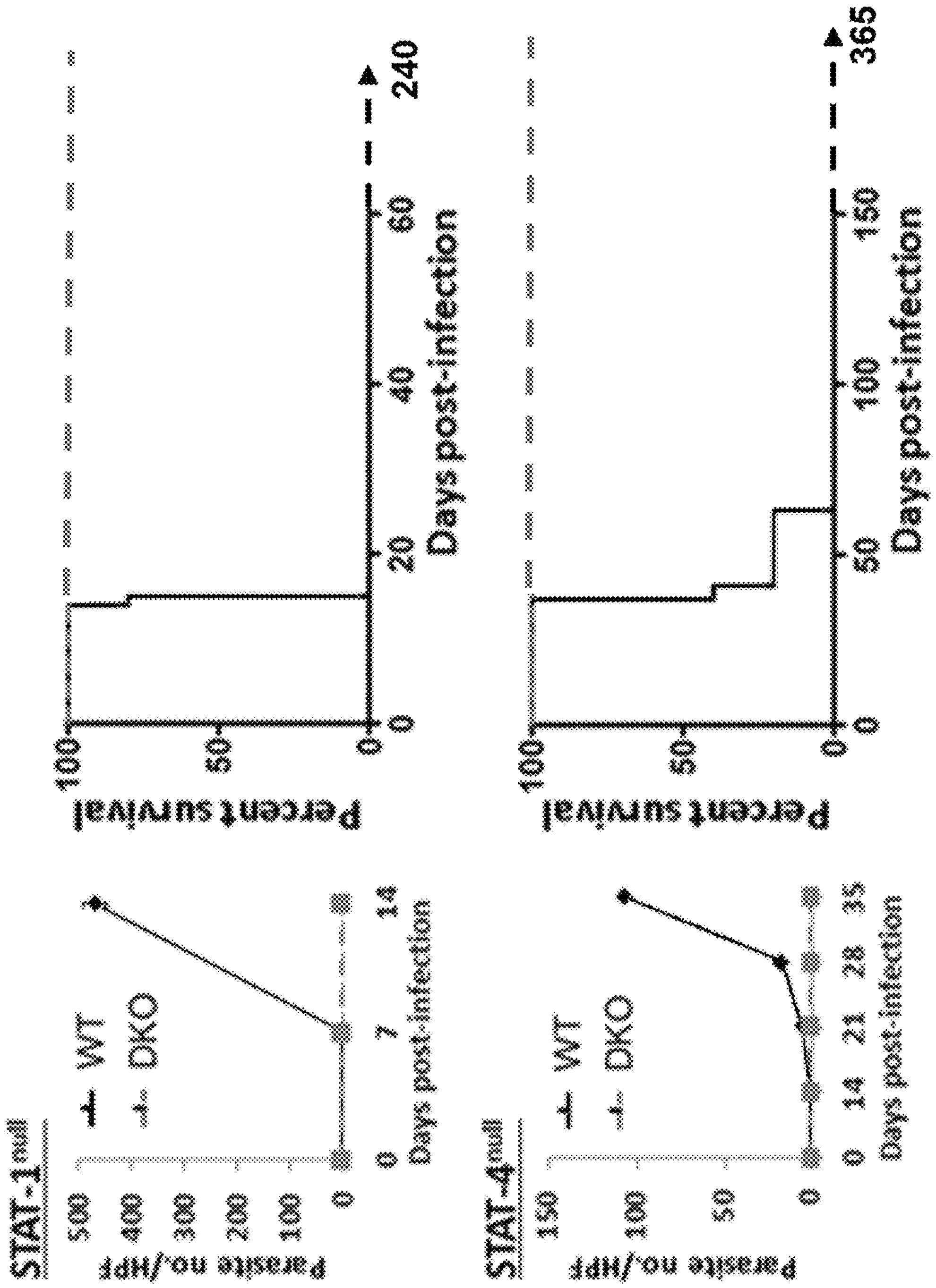
FIG. 2A contains parasitemia (left) and survival curves (right) of experimental infections of STAT-$1^{null}$ (upper panels) and STAT-$4^{null}$ (lower panels) strains of mice with WT and DKO parasites lines.
Figure 2B:
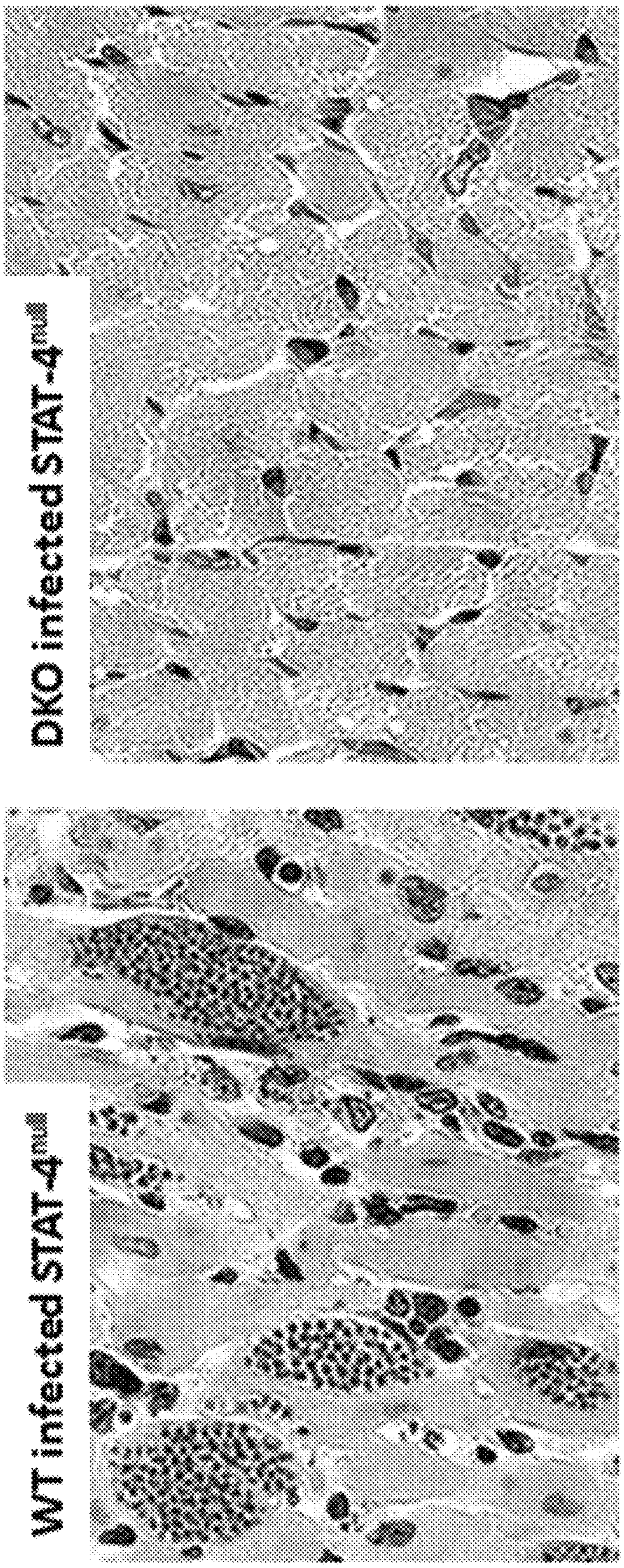
FIG. 2B is a comparison of heart tissue harvested from STAT-$4^{null}$ mice, showing heavy parasitization by WT parasites but not disease in DKO-infected animals.
Figure 2C:
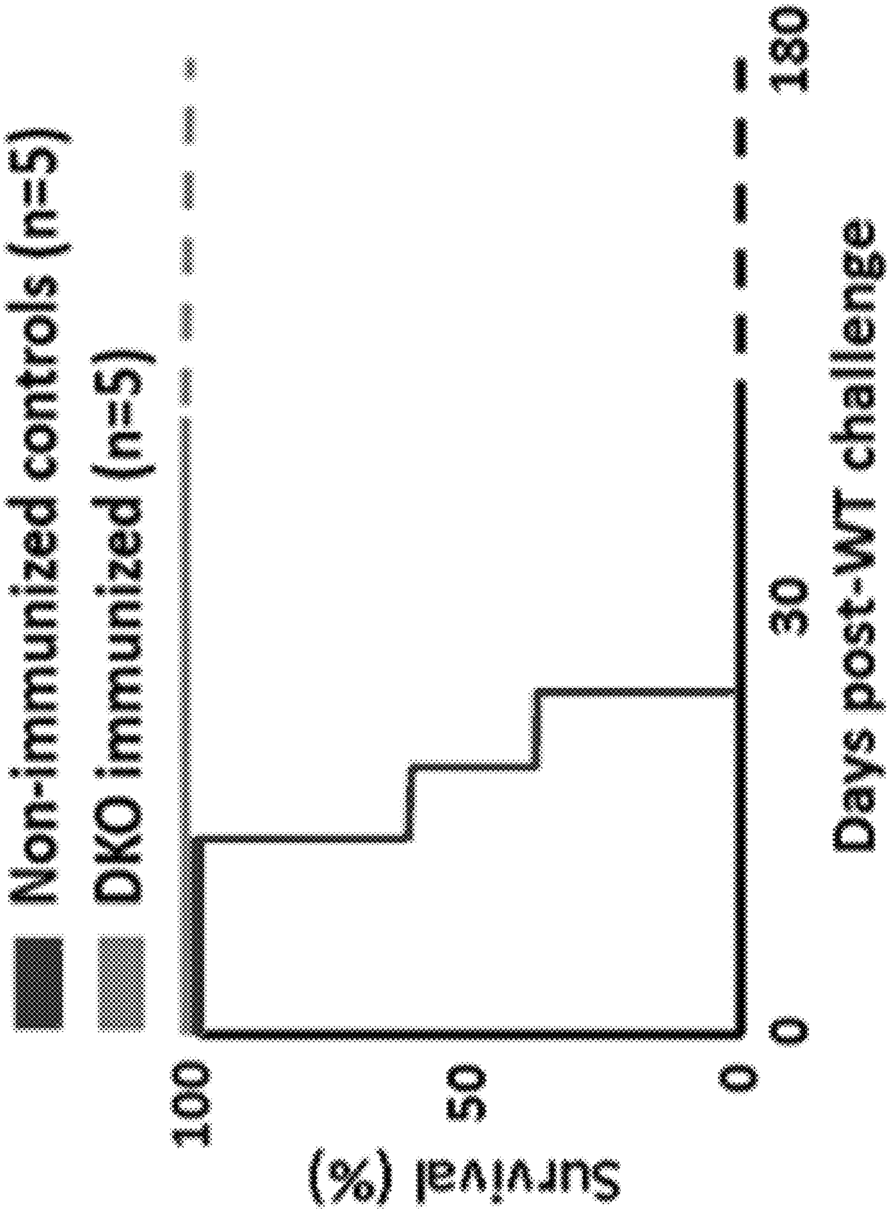
FIG. 2C shows repeat immunization of DKO elicits an immune response and confers protection.

Example 1: Construction and Testing of Cyp 19 Knock-Out Mutant Parasite Line In order to characterize the effects of Cyp19 during infection a Cyp19 double allelic knock-out (DKO) mutant was created by homologous recombination (strategy shown in FIG. 1A). Integration of selectable antibiotic resistance markers were verified by PCR and loss of Cyp19 verified by Western blotting (FIG. 1B), indicated DKO parasites are completely devoid of Cyp19 expression. Infection of rat heart myoblasts (RHMs, line H9C2) with WT, single knock-outs (SKO) and DKO parasites (FIG. 1C) indicate that WT parasites were able to infect the cells forming amastigotes and subsequently differentiating into and exiting cells as trypomastigotes, whereas DKO parasites formed very scanty number of amastigotes which later degenerated inside the RHM and failed to give rise to productive infection a formation and release of trypomastigotes. Infections with SKO parasites with partial expression of Cyp19 progressed slower but were able to productively infect cells. Infection of immune-deficient mice (either STAT-$1^{-/-}$ or STAT-$4^{-/-}$) serves as a robust test of parasite pathogenesis and infection and were used for comparative infection of WT and Cyp19-DKO lines (FIG. 2). Either mouse strain infected with the Cyp19-DKO parasites had no mortality, detectable parasitemia or tissue pathology whereas mice infected with the WT parasites died between 2-4 weeks post-infection and had detectable growth of parasites in the blood and cardiac tissue. Repeated immunization of DKO with TcCyp19-/- confers protection against virulent challenge (FIG. 2C and Table 1).

TABLE 1

| Explantation parasite recovery from WT parasite challenged A/J mice pre-immunized with DKO parasites | | |
|---|---|---|
| Tissue | Non-immunized (n = 5) | Immunized (n = 5) |
| Heart | 5/5 | 0/5 |
| Liver | 2/5 | 0/5 |
| GI mesentery | 3/5 | 0/5 |
| Stomach | 2/5 | 0/5 |
| Large Intestine | 1/5 | 0/5 |
| Spleen | 5/5 | 0/5 |
| Blood | 5/5 | 0/5 |

* Explant of tissue (10 days or 6 months post-infection with WT parasites for non-immunized mice or DKO-immunized mice, respectively) into LDNT for 30 days and microscopic identification of motile epimastigotes.

Example 2: Development of Anti-Parasite Immunity Induced by the DKO Strain

Figure 3B:
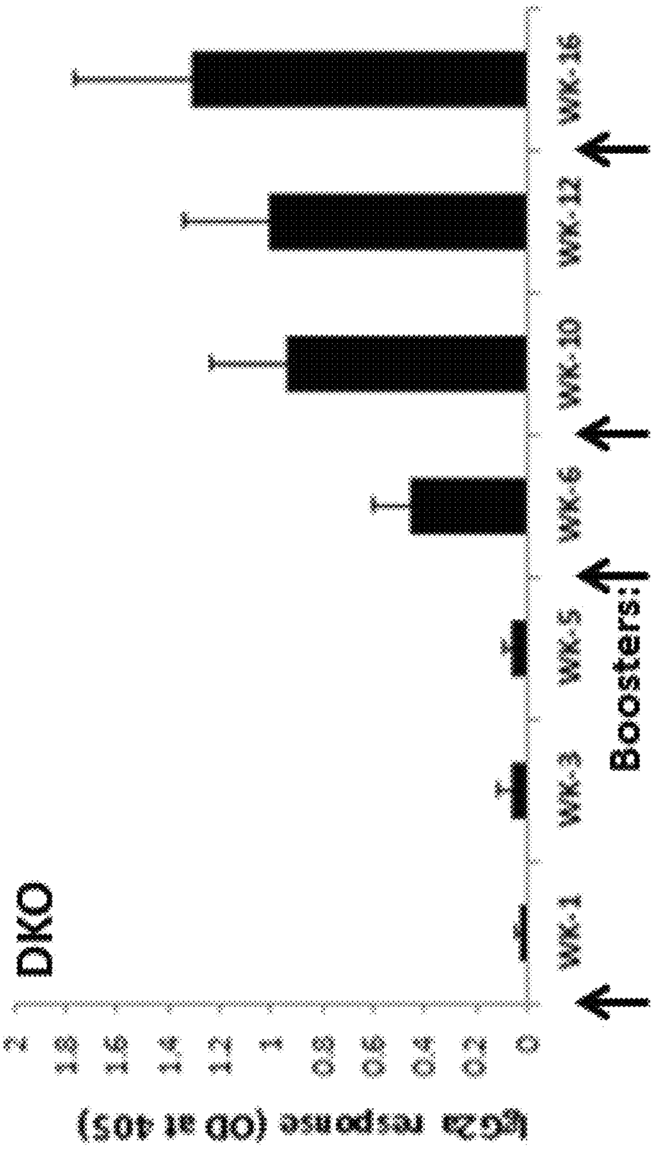
FIGS. 3A and 3B are bar graphs showing stimulation of anti-*T. cruzi* antibodies by WT (FIG. 3A) and $cyp19^{-/-}$ (DKO) (FIG. 3B) parasites in immune-competent A/J mice. Mice (n=4) were infected with either WT or DKO parasites. Single inoculation of WT parasites (FIG. 3A, arrow) induce a robust and escalating immunity due to their in vivo replication. Repeated infections with DKO parasites (FIG. B, arrows) are not deleterious to mice and result in increasing immunity to parasite antigens as measured by quantitative *T. cruzi* IgGa ELISA. All infections were with $10^5$ parasites IP. Values are mean−/+std deviation.
Figure 3A:
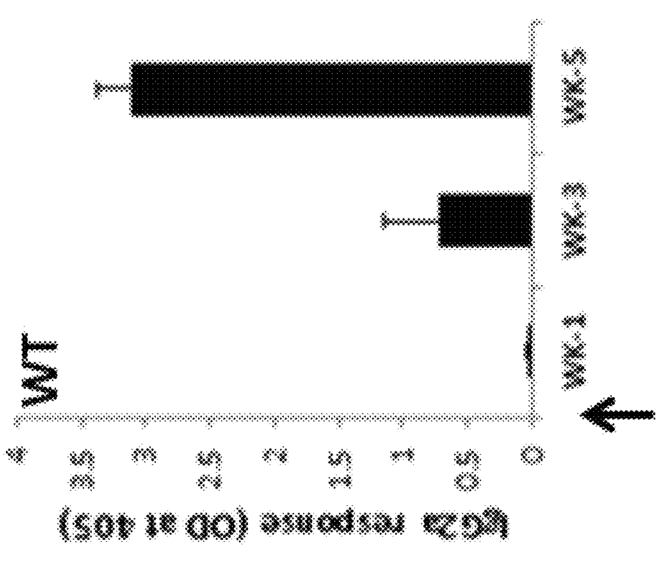
Figures 3C, 3D, 3E:
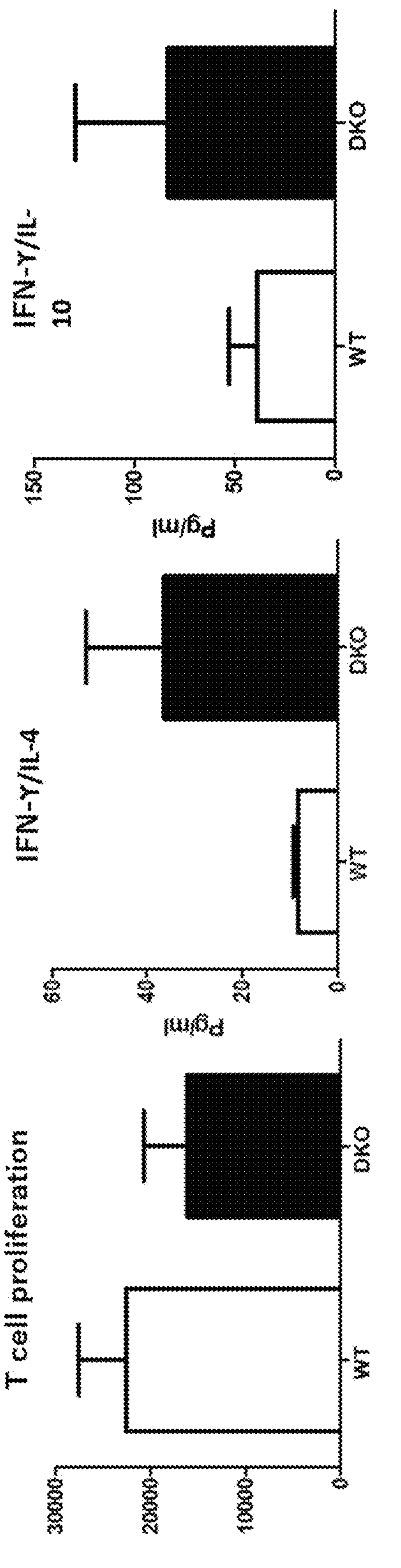
FIGS. 3C to 3E show $TcCyp19^{-/-}$ vaccination induces protective parasite-specific Th1 dominant response.

This Example tests whether the anti-parasite immunity produced by the DKO strain is protective against challenge by WT parasites. There is currently no vaccine available for Chagas disease, therefore the finding of protection by the DKO line would be highly significant and a big step forward in development of a protective vaccine against Chagas cardiomyopathy. While the DKO parasite line does not replicate in or cause disease in host animals (FIG. 2) it does produce increasing anti-*T. cruzi* antibodies when repeatedly inoculated into immune-competent mice (FIGS. 3A-3B). Immunization with TcCyp19$^{-/-}$ also elicits parasite-specific T cell responses (FIGS. 3C-3E).

Example 3: Challenge of DKO-Immunized Animals Demonstrated Protection

Figure 4B:
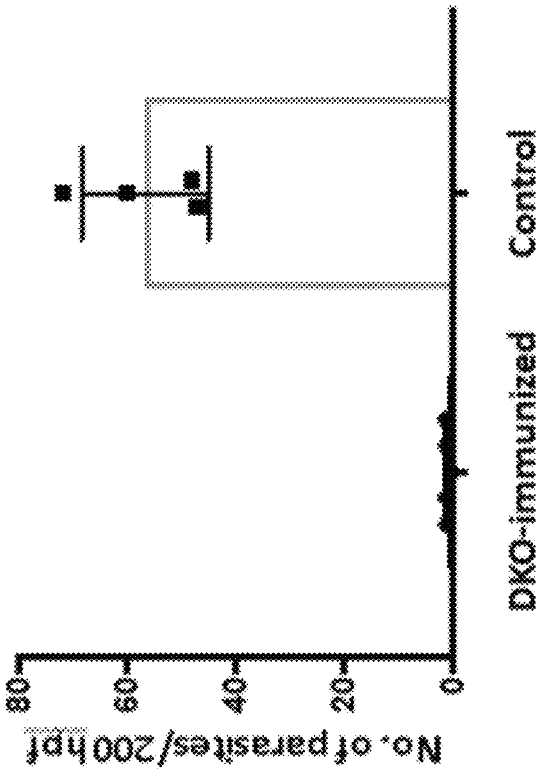
FIGS. 4A and 4B show $Cyp19^{-/-}$ (DKO)-immunized mice are protected from death due to *T. cruzi* infection.
Figure 4A:
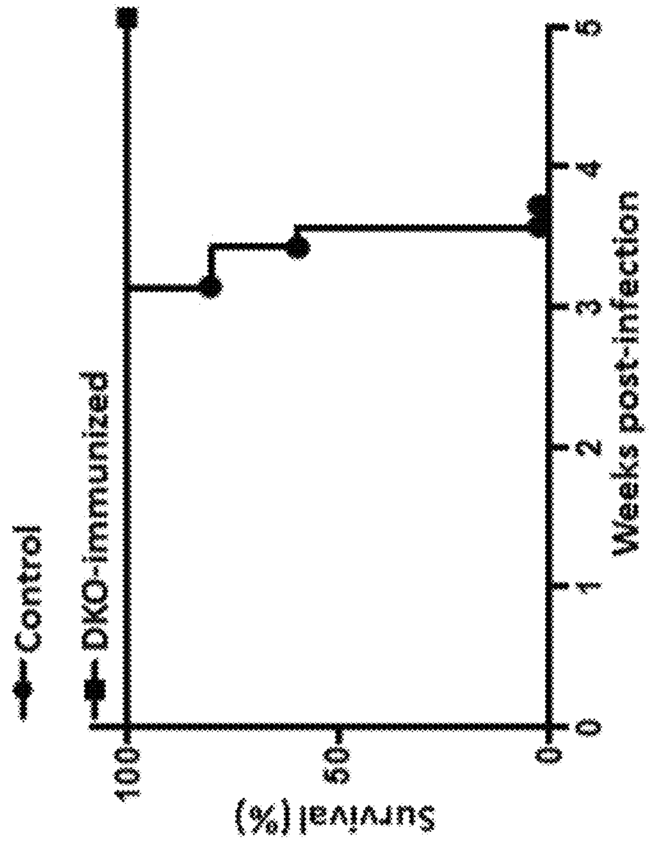
Figure 5:
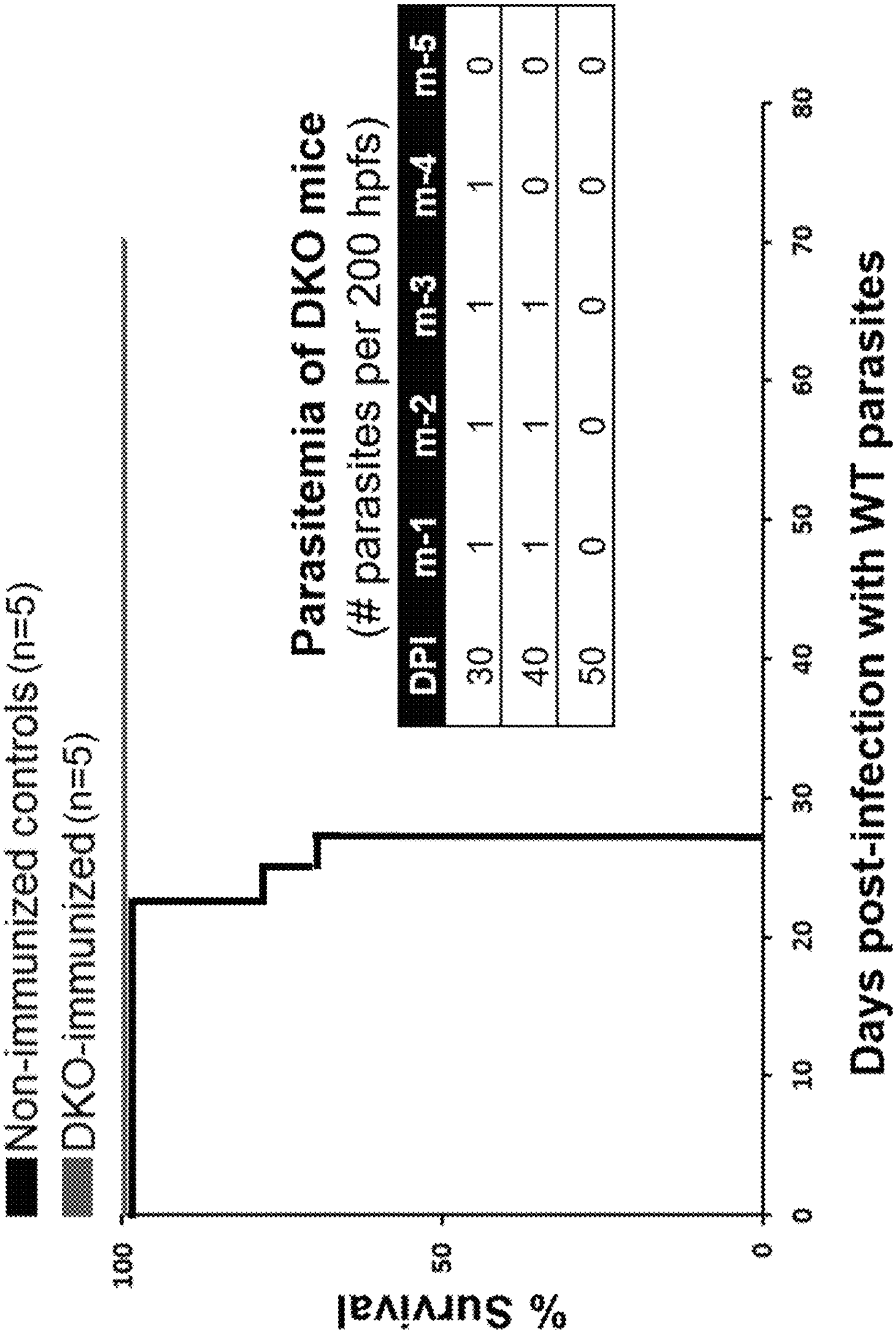
FIG. 5 shows that $Cyp19^{-/-}$ (DKO)-immunized mice are protected against WT-TC infection.

Mice immunized with DKO parasites were challenged with virulent wildtype parasites. Non-immunized control mice died between 3-4 weeks post-infection whereas DKO-immunized mice survive through week 5 post infection (FIG. 4A). Analysis of parasitemia in both groups demonstrates that the DKO-immunized mice have significantly reduced parasitemia whereas control mice have significantly elevated parasitemia just prior to death (FIG. 4B).

Example 4: Single-Dose DKO Vaccination is Protective

Figure 6A:
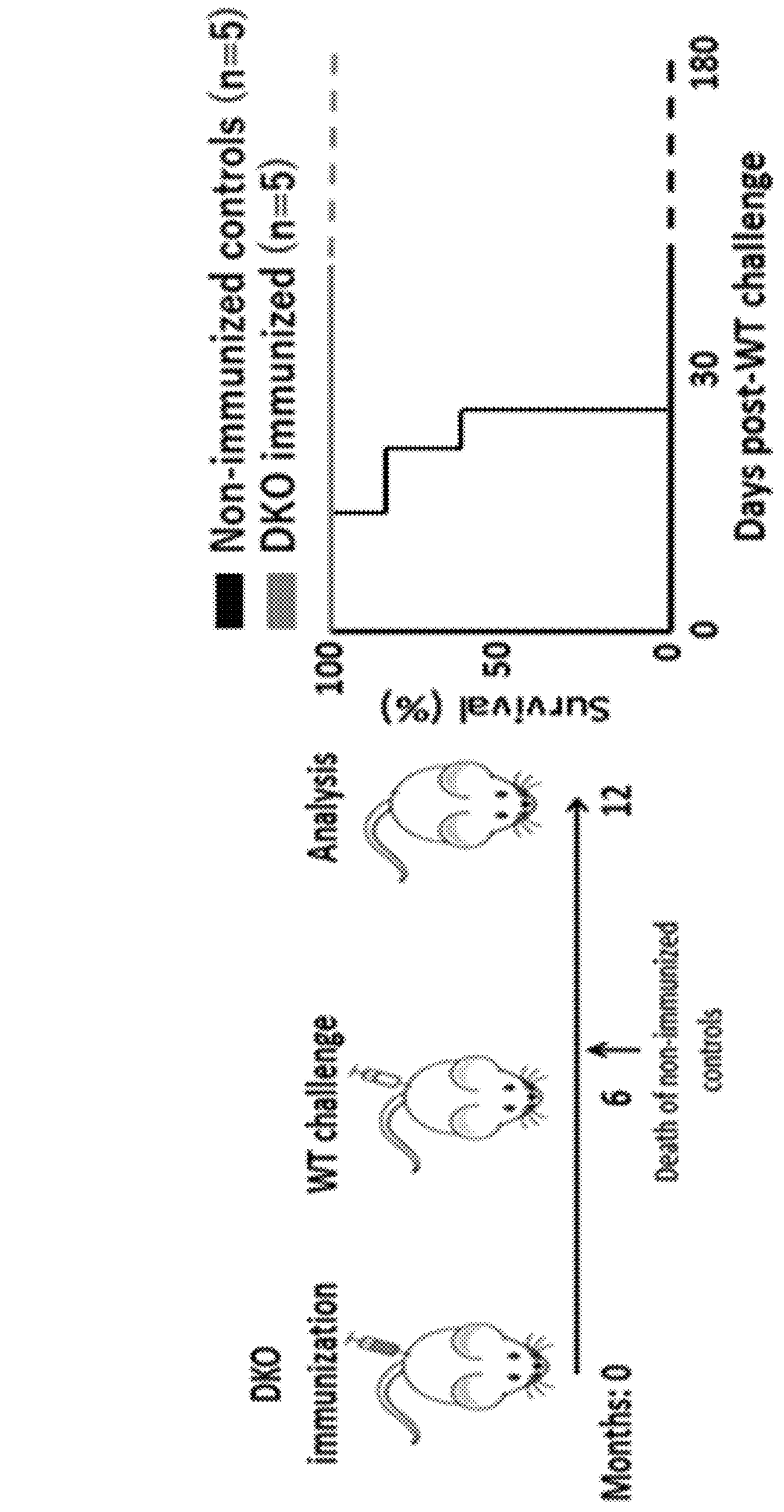
FIGS. 6A and 6B show single dose DKO vaccination is protective.
Figure 6B:
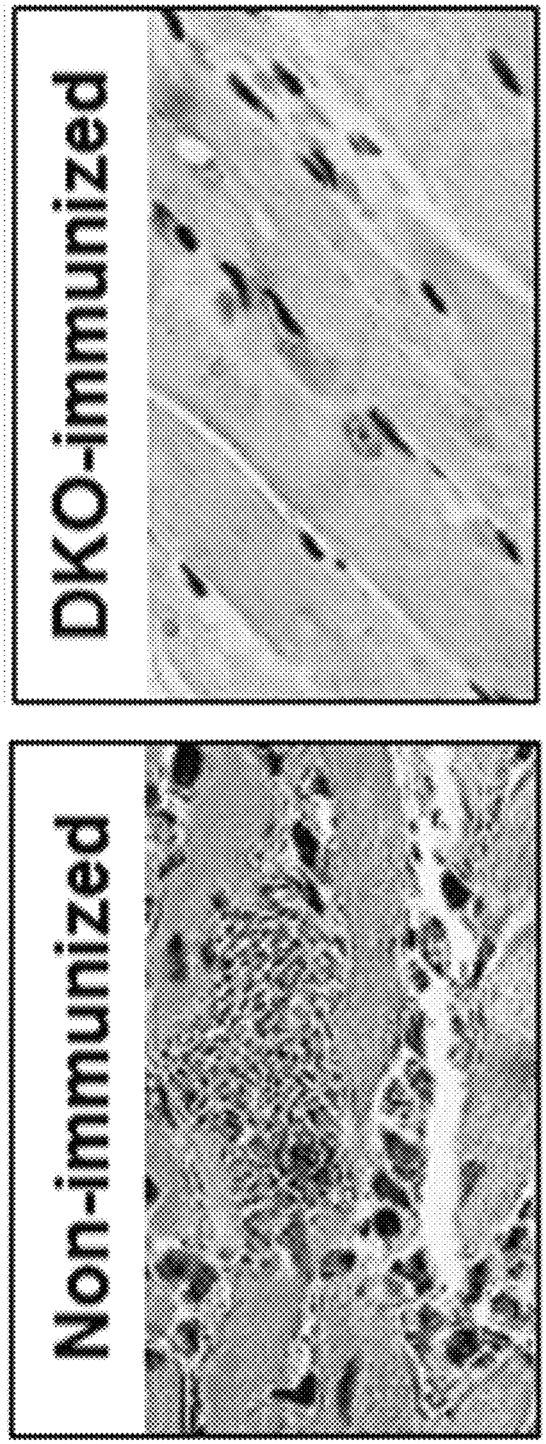

As shown in FIGS. 6A-6B and Table 2, a single dose of DKO vaccination is protective.

TABLE 2

| Explantation parasite recovery from WT parasite challenged A/J mice pre-immunized with single dose of DKO parasites | | |
|---|---|---|
| Tissue | Non-immunized (n = 5) | Immunized (n = 5) |
| Heart | 5/5 | 0/5 |
| Liver | 2/5 | 0/5 |
| GI mesentery | 3/5 | 0/5 |
| Stomach | 2/5 | 0/5 |
| Large Intestine | 1/5 | 0/5 |
| Spleen | 5/5 | 0/5 |
| Blood | 5/5 | 0/5 |

* Explant of tissue (10 days or 6 months post-infection with WT parasites for non-immunized mice or DKO-immunized mice, respectively) into LDNT for 30 days and microscopic identification of motile epimastigotes.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

What is claimed is:

1. An avirulent live vaccine, comprising a recombinant protozoan from the order Trypanosomatida having a knocked out or silenced cyclophilin 19 (cyp19) gene.

2. The vaccine of claim 1, wherein the protozoan is from the genus *Trypanosoma*.

3. The vaccine of claim 2, wherein the protozoan is *Trypanosoma cruzi* or *Trypanosoma brucei*.

4. The vaccine of claim 1, wherein the protozoan is from the genus *Leishmania*.

5. The vaccine of claim 1, comprising a double knockout of the cyclophilin gene.

6. A method for inducing a protective immune response in a subject, comprising administering to the subject the vaccine of claim 1.

7. A method of treating Chagas disease in a subject, comprising administering to the subject the vaccine of claim 1.

8. A method of treating African trypanosomiasis in a subject, comprising administering to the subject the vaccine of claim 1.

9. A method of treating leishmaniasis in a subject, comprising administering to the subject the vaccine of claim 1.

* * * * *

SEQUENCE LISTING

```
<160> NUMBER OF SEQ ID NOS: 4

<210> SEQ ID NO 1
<211> LENGTH: 1098
<212> TYPE: DNA
<213> ORGANISM: Trypanosoma cruzi

<400> SEQUENCE: 1

gctatattgg gtagctcagt gagcatttta catctttcta aaagggaatt aatttattaa      60

caacacacaa tgtcgtacaa gccgcatcac gccaccgtac cgaccaaccc gaaggtcttc     120

ttcgacgtca gcattggtgg ccaatcagcc ggacgtgttg tcttcgagct cttcgccgac     180

gccgttccca agacggctga gaacttccgg gcactttgca ccggtgagaa gaactttggc     240

tacgctggaa gcggctttca tcgcattatc ccccagttca tgtgccaggg gggtgacttc     300

accaatcaca acggcactgg cggcaggtct atctacggtg agaaatttgc cgacgagtcc     360

tttgctggca aggctggcaa gcacttcggc ctcggtacgc tttccatggc gaatgctggc     420

ccaaatacta acggctccca gttctttatt tgcactgcac ccacacagtg gcttgacggc     480

aagcatgtcg tctttggcca ggtgctggaa ggcattgaag tcgttaaggc aatggaagcc     540

gttggctccc agacgggcaa gacgagcaag ccggtgaaga ttgaggcctc tggtcaactt     600

taaactgctc ttccggcaga gctttgaatg gacaaataac cggaaaagaa gggtacgggg     660
```

```
aggagggacc aaaattagat taatccaaga accagaaaag aaaggaaaag gaaagaaaag    720

agaaaaaaga aataatatga gaaaatgaga ataacgaggg tgtgaaaatc tgacttaaca    780

gatccagccc gtgagatggc aataaggcag gaggcaaagc gagaaaaagc gtgctctcac    840

gcctaagaaa gagggaagaa gagaggaagg tggagaaaaa tttcttaagg gtctgaaaaa    900

agggagaggg ggaaaaaaaa aagatgaaga caaagggaaa aaggggctaa aacgcggaaa    960

aaaaaaagta caggaagaag tggactcatg tgcacccagg agggaaaaaa aaagggaatt   1020

gaatggccat gtacttcttg cctaattatt ttgctgttgg gtttttatta aaaaaaaaaa   1080

aaaaaaaaaa aaaaagtt                                                 1098


<210> SEQ ID NO 2
<211> LENGTH: 177
<212> TYPE: PRT
<213> ORGANISM: Trypanosoma cruzi

<400> SEQUENCE: 2

Met Ser Tyr Lys Pro His His Ala Thr Val Pro Thr Asn Pro Lys Val
1               5                   10                  15

Phe Phe Asp Val Ser Ile Gly Gly Gln Ser Ala Gly Arg Val Val Phe
            20                  25                  30

Glu Leu Phe Ala Asp Ala Val Pro Lys Thr Ala Glu Asn Phe Arg Ala
        35                  40                  45

Leu Cys Thr Gly Glu Lys Asn Phe Gly Tyr Ala Gly Ser Gly Phe His
    50                  55                  60

Arg Ile Ile Pro Gln Phe Met Cys Gln Gly Gly Asp Phe Thr Asn His
65                  70                  75                  80

Asn Gly Thr Gly Gly Arg Ser Ile Tyr Gly Glu Lys Phe Ala Asp Glu
                85                  90                  95

Ser Phe Ala Gly Lys Ala Gly Lys His Phe Gly Leu Gly Thr Leu Ser
            100                 105                 110

Met Ala Asn Ala Gly Pro Asn Thr Asn Gly Ser Gln Phe Phe Ile Cys
        115                 120                 125

Thr Ala Pro Thr Gln Trp Leu Asp Gly Lys His Val Val Phe Gly Gln
    130                 135                 140

Val Leu Glu Gly Ile Glu Val Val Lys Ala Met Glu Ala Val Gly Ser
145                 150                 155                 160

Gln Thr Gly Lys Thr Ser Lys Pro Val Lys Ile Glu Ala Ser Gly Gln
                165                 170                 175

Leu


<210> SEQ ID NO 3
<211> LENGTH: 1087
<212> TYPE: DNA
<213> ORGANISM: Trypanosoma brucei

<400> SEQUENCE: 3

aactaacgct attattagaa cagtttctgt actatattgg tcgttgaaac cacctatacc     60

tatactattt cgcataagat gtcatacagg ccccaccacg caactgtacc caccaatccc    120

aaggtgtact ttgatgtgag cattgcaggt caggcagccg gccgcatcac ctttgagctc    180

ttcgctgacg ccgtaccaaa gacggcggag aacttccgtg cgttatgcac tggtgagaag    240

ggcttcgggt acgccggcag cggctttcat cgcatcattc cgcaattcat gtgccaaggt    300

ggtgacttca ctcgccacaa tggcacatgc ggcaagtcca tctatggtga aaagttcccc    360
```

-continued

```
gatgaaagct tcgccggaaa ggcgggtaaa cacttcggcg ctggcacgct ttccatggcc    420

aacgctggcc ccaacacgaa cggttcccag ttcttcattt gcacggctcc cactcagtgg    480

cttgacggca aacacgtcgt cttcggtcag gtgcttgaag gcatggacgt cgtcaaggca    540

atggaagctg tcggctcgca agggggaagc acaagcaagc ccgtcaagat tgactcgtgc    600

ggccaactat aagagagcac gtagaggcgt gcacatgcaa catgaaatta cgctccgatc    660

ccactgcttc cccccctcc ccgtactgat acacgcacag cgaacaccga ctaatttttt    720

tttccctcaa gagtgcaagt tgaaaagggg aaaagcaagc agtaaaaggg acaaaggaga    780

ttattaaaag cagaggagca aataaaaaaa aaagaaatga aatgaataag caaaagaaaa    840

tctctggctt ccaaatgaaa aaggaaaaga agaaaacata tggtacgtca tattctttga    900

ggacggtttg ctggagaaaa gaacaaataa atgacaattt cttatggtta aagaaaaaga    960

agaagaaaga aacagaagat agagaattgt cataaataag tgaaagatgg gaggggacaa   1020

agtaattaag tgggagtcat actgcgggga gtaccacaag gggaaaaatg ctagggatga   1080

aacgaaa                                                             1087


<210> SEQ ID NO 4
<211> LENGTH: 177
<212> TYPE: PRT
<213> ORGANISM: Trypanosoma brucei

<400> SEQUENCE: 4

Met Ser Tyr Arg Pro His His Ala Thr Val Pro Thr Asn Pro Lys Val
1               5                   10                  15

Tyr Phe Asp Val Ser Ile Ala Gly Gln Ala Ala Gly Arg Ile Thr Phe
            20                  25                  30

Glu Leu Phe Ala Asp Ala Val Pro Lys Thr Ala Glu Asn Phe Arg Ala
        35                  40                  45

Leu Cys Thr Gly Glu Lys Gly Phe Gly Tyr Ala Gly Ser Gly Phe His
    50                  55                  60

Arg Ile Ile Pro Gln Phe Met Cys Gln Gly Gly Asp Phe Thr Arg His
65                  70                  75                  80

Asn Gly Thr Cys Gly Lys Ser Ile Tyr Gly Glu Lys Phe Pro Asp Glu
                85                  90                  95

Ser Phe Ala Gly Lys Ala Gly Lys His Phe Gly Ala Gly Thr Leu Ser
            100                 105                 110

Met Ala Asn Ala Gly Pro Asn Thr Asn Gly Ser Gln Phe Phe Ile Cys
        115                 120                 125

Thr Ala Pro Thr Gln Trp Leu Asp Gly Lys His Val Val Phe Gly Gln
    130                 135                 140

Val Leu Glu Gly Met Asp Val Val Lys Ala Met Glu Ala Val Gly Ser
145                 150                 155                 160

Gln Gly Gly Ser Thr Ser Lys Pro Val Lys Ile Asp Ser Cys Gly Gln
                165                 170                 175

Leu
```